(12) United States Patent
Toudou et al.

(10) Patent No.: US 10,309,923 B2
(45) Date of Patent: Jun. 4, 2019

(54) GAS SENSOR DEVICE

(71) Applicant: DENSO CORPORATION, Kariya, Aichi-pref. (JP)

(72) Inventors: Yuusuke Toudou, Kariya (JP); Takehito Kimata, Kariya (JP); Mitsunobu Nakatou, Nishio (JP)

(73) Assignee: DENSO CORPORATION, Kariya (JP)

( * ) Notice: Subject to any disclaimer, the term of this patent is extended or adjusted under 35 U.S.C. 154(b) by 171 days.

(21) Appl. No.: 15/325,206

(22) PCT Filed: Jul. 8, 2015

(86) PCT No.: PCT/JP2015/069694
§ 371 (c)(1),
(2) Date: Jan. 10, 2017

(87) PCT Pub. No.: WO2016/006635
PCT Pub. Date: Jan. 14, 2016

(65) Prior Publication Data
US 2017/0191957 A1    Jul. 6, 2017

(30) Foreign Application Priority Data

Jul. 10, 2014 (JP) ................................ 2014-141891
Apr. 9, 2015 (JP) ................................ 2015-079765

(51) Int. Cl.
*G01N 27/407*     (2006.01)
*G01N 27/41*      (2006.01)
(52) U.S. Cl.
CPC .......... *G01N 27/41* (2013.01); *G01N 27/4071* (2013.01); *G01N 27/4074* (2013.01)

(58) Field of Classification Search
CPC .................... G01N 27/4071; G01N 27/4072
See application file for complete search history.

(56) References Cited

U.S. PATENT DOCUMENTS 5,672,811 A    9/1997  Kato et al. ............... 73/31.05
5,866,799 A    2/1999  Kato et al. ............... 73/31.05
(Continued)

FOREIGN PATENT DOCUMENTS

JP    2000-321238     11/2000
JP    2003-149199      5/2003
(Continued)

*Primary Examiner* — Alexander S Noguerola
(74) *Attorney, Agent, or Firm* — Nixon & Vanderhye PC

(57) ABSTRACT

A gas sensor device is equipped with the sensor cell, the pump cell, the inner void space, and the gas inlet. The sensor cell is created by a portion of the solid electrolyte body and a pair of sensor electrodes disposed on the solid electrolyte body. The pump cell is created by a portion of the solid electrolyte body and a pair of pump electrodes disposed on the solid electrolyte body. The inner void space faces the sensor electrode and the pump electrode. If a dimension of said gas inlet in a direction in which the measurement gas flows in the gas inlet is defined as L1, a sectional area of the gas inlet taken perpendicular to the direction of flow of the measurement gas in the gas inlet is defined as S1, a distance between the gas inlet and the sensor cell is defined as L2, and a sectional area of the inner void space taken perpendicular to a direction in which the pump cell and the sensor cell are aligned with each other is defined as S2, a relation of $1000 \leq (L1/S1) \times (L2/S2) \leq 5000$ is met.

3 Claims, 6 Drawing Sheets

(56) References Cited

U.S. PATENT DOCUMENTS

| | | | |
|---|---|---|---|
| 5,939,615 A | 8/1999 | Kato et al. | 73/31.05 |
| 6,076,393 A | 6/2000 | Kato et al. | 73/31.05 |
| 6,196,053 B1 | 3/2001 | Kato et al. | 73/31.05 |
| 6,551,497 B1 * | 4/2003 | Gao | G01N 27/4065 204/425 |
| 2009/0229978 A1 | 9/2009 | Mizutani et al. | 73/31.05 |
| 2011/0083490 A1 | 4/2011 | Murakami et al. | 73/31.05 |

FOREIGN PATENT DOCUMENTS

| | | |
|---|---|---|
| JP | 2011-58834 | 3/2011 |
| JP | 2012-052901 | 3/2012 |

\* cited by examiner

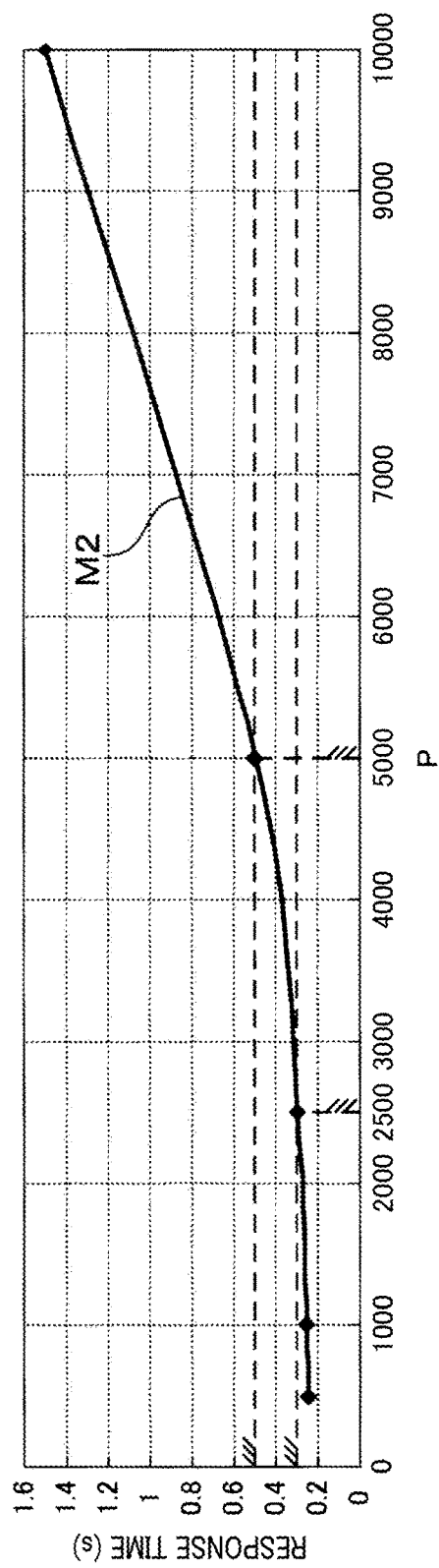

GAS SENSOR DEVICE

This application is the U.S. national phase of International Application No. PCT/JP2015/069694 filed Jul. 8, 2015 which designated the U.S. and claims priority to JP Patent Application No. 2014-141891 filed Jul. 10, 2014 and JP Patent Application No. 2015-079765 filed Apr. 9, 2015, the entire contents of each of which are hereby incorporated by reference.

TECHNICAL FIELD

The present invention generally relates to a gas sensor device which measures the concentration of a given gas component contained in measurement gas.

BACKGROUND ART

As gas sensor devices to measure the concentration of a given gas component in a measurement gas, there are ones equipped with a pump cell working to control the concentration of oxygen contained in measurement gas taken thereinto. The control of the concentration of oxygen by the pump cell avoids an error in determining the concentration of the given gas component using a sensor cell of the gas sensor device which arises from oxygen contained in the measurement gas.

Japanese Patent First Publication No. 8-271476 discloses a gas sensor device which is equipped with a first inner void from which a pump cell discharges oxygen in a measurement gas and a second inner void in which a sensor cell measures the concentration of a given gas component of the measurement gas. The gas sensor device also includes a first diffusion rate controlling path in which the measurement gas introduced into the first inner void is controlled in diffusion rate thereof and a second diffusion rate controlling path provided between the first inner void and the second inner void.

SUMMARY OF THE INVENTION

Problem to be Solved by the Invention

In the above structure, however, the measurement gas, as introduced from outside the gas sensor device, passes through the first and second diffusion rate controlling paths until it reaches the second inner void in which the sensor cell is disposed, thus resulting in an increase in diffusion distance, which will lead to a difficulty in improving the responsiveness of the gas sensor device.

The diffusion resistance in the diffusion rate controlling paths may be decreased in order to improve the responsiveness, but however, it will result in a deterioration of measurement accuracy. Specifically, the decrease in diffusion resistance in the first diffusion rate controlling path will cause a great deal of measurement gas to be introduced into the first inner void, thus resulting in a lack in controlling the concentration of oxygen in the measurement gas. Further, the decrease in diffusion resistance in the second diffusion rate controlling path will result in a lack in controlling the concentration of oxygen in the first inner void before it reaches the second inner void, thus resulting in a deterioration of the measurement accuracy.

The present invention was made in view of the above background and provides a gas sensor device which is capable of ensuring compatibility between the responsiveness and the measurement accuracy.

Means for Solving the Problem

According to one embodiment of the invention, there is provided a gas sensor device which comprises: (a) a sensor cell which is made up of a first portion of an oxygen ion conductive solid electrolyte body and a pair of sensor electrodes disposed on the solid electrolyte body, the sensor cell working to measure a concentration of a given gas component in a measurement gas; (b) a pump cell which is made up of a second portion of the solid electrolyte body and a pair of pump electrodes disposed on the solid electrolyte body, the pump cell working to regulate a concentration of oxygen in the measurement gas; (c) an inner void space which faces one of the sensor electrodes and one of the pump electrodes and into which the measurement gas is introduced; and (d) a gas inlet through which the measurement gas is introduced into said inner void space and which is shaped to provide a given diffusion resistance to the measurement gas introduced into said inner void space. If a dimension of said gas inlet in a direction in which the measurement gas flows in said gas inlet is defined as L1, a sectional area of said gas inlet taken perpendicular to the direction of flow of the measurement gas in said gas inlet is defined as S1, a distance between said gas inlet and said sensor cell is defined as L2, and a sectional area of said inner void space taken perpendicular to a direction in which said pump cell and said sensor cell (2) are aligned with each other is defined as S2, a relation of $1000 \leq (L1/S1) \times (L2/S2) \leq 5000$ is met.

Effect of the Invention

The above gas sensor device is designed to have a relation of $1000 \leq (L1/S1) \times (L2/S2) \leq 5000$, thus ensuring compatibility between the responsiveness and the measurement accuracy.

The inventors of this application have focused on the fact that the responsiveness and the measurement accuracy greatly depend upon the structure of the gas inlet as well as that of the inner void space. The greater (L1/S1) is, the greater the diffusion resistance in the gas inlet. Accordingly, in this specification, (L1/S1) will also be referred to as a first diffusion resistance indicator for descriptive purposes. The greater the first diffusion resistance indicator, the lower a rate at which the measurement gas is introduced into the inner void space. This results in a decrease in the responsiveness, but however, the measurement accuracy is improved because the amount of oxygen the pump cell is required to regulate is decreased.

The greater (L2/S2) is, the greater the diffusion resistance to which the measurement gas introduced into the inner void space is subjected until it reaches the sensor electrodes. Accordingly, in this specification, (L2/S2) will also be referred to as a second diffusion resistance indicator for descriptive purposes. The greater the second diffusion resistance indicator, the longer the time it takes for the measurement gas introduced into the inner void space to reach the sensor electrodes. This results in a decrease in the responsiveness, but however, the measurement accuracy is improved because the time required by the pump cell to regulate oxygen is decreased.

As apparent from the above discussion, the first diffusion resistance indicator and the second diffusion resistance indicator are slightly different from each other in principle to effect the responsiveness and the measurement accuracy, but they are the same in that the greater each of the first and second diffusion resistance indicators, the lower the responsiveness, but the higher the measurement accuracy. The inventors, therefore, checked a relation of a product of the first diffusion resistance indicator and the second diffusion resistance indicator to each of the responsiveness and the measurement accuracy (see experimental examples 1 and 2 which will be described later) and found that the compatibility between the responsiveness and the measurement accuracy is achieved by selecting the product of the first diffusion resistance indicator and the second diffusion resistance indicator, i.e., $(L1/S1) \times (L2/S2)$ to fall in a range of 1000 to 5000.

As described above, the present invention provides a gas sensor device which is capable of ensuring the compatibility between the responsiveness and the measurement accuracy.

BRIEF DESCRIPTION OF THE DRAWINGS

FIG. 6 is a diagrammatic view which represents a relation between a product P and a response time in the experimental example 2.

EMBODIMENTS FOR CARRYING OUT THE INVENTION

In the above gas sensor device, it is advisable that a relation of $1250 \leq (L1/S1) \times (L2/S2) \leq 2500$ be satisfied. This ensures a greater degree of compatibility between the responsiveness and the measurement accuracy.

In this specification, the product of the first diffusion resistance indicator and the second diffusion resistance indicator will also be expressed by P. Note that $(L1/S1) \times (L2/S2) = P$.

The above gas inlet may be made of a porous body. In this case, the sectional area S1 is defined by a product of a sectional area of the porous body and a porosity of the porous body. This facilitates adjustment of the diffusion resistance in the gas inlet. The adjustment of $(L1/S1) \times (L2/S2)$ enables the responsiveness and the measurement accuracy to be accurately controlled.

It is advisable that the above inner void space be shaped to have a configuration uniform from a region where the inner void space faces the pump electrode to a region where the inner void space faces the sensor electrode. This achieves a smooth travel of the measurement gas introduced into the inner void space to the sensor electrode, thereby enhancing the responsiveness of the gas sensor device.

In the case where a sectional area of the inner void space taken perpendicular to a direction in which the pump cell and the sensor cell are aligned with each other changes in the direction of alignment of the pump cell and the sensor cell, a minimum sectional area of the inner void space between the gas inlet and the sensor cell is defined as the above sectional area S2. The dimension L1 of the gas inlet is a dimension of the gas inlet in a direction of low of the measurement gas in the gas inlet. In the case where a sectional area of the gas inlet taken perpendicular to a direction in which the measurement gas flows in the gas inlet changes in the direction of flow of the measurement gas, a minimum sectional area of the gas inlet is defined as the above sectional area S1.

EMBODIMENT

Embodiment 1

An embodiment of the above gas sensor device will be described below using FIGS. 1 to 4.

Figure 1:
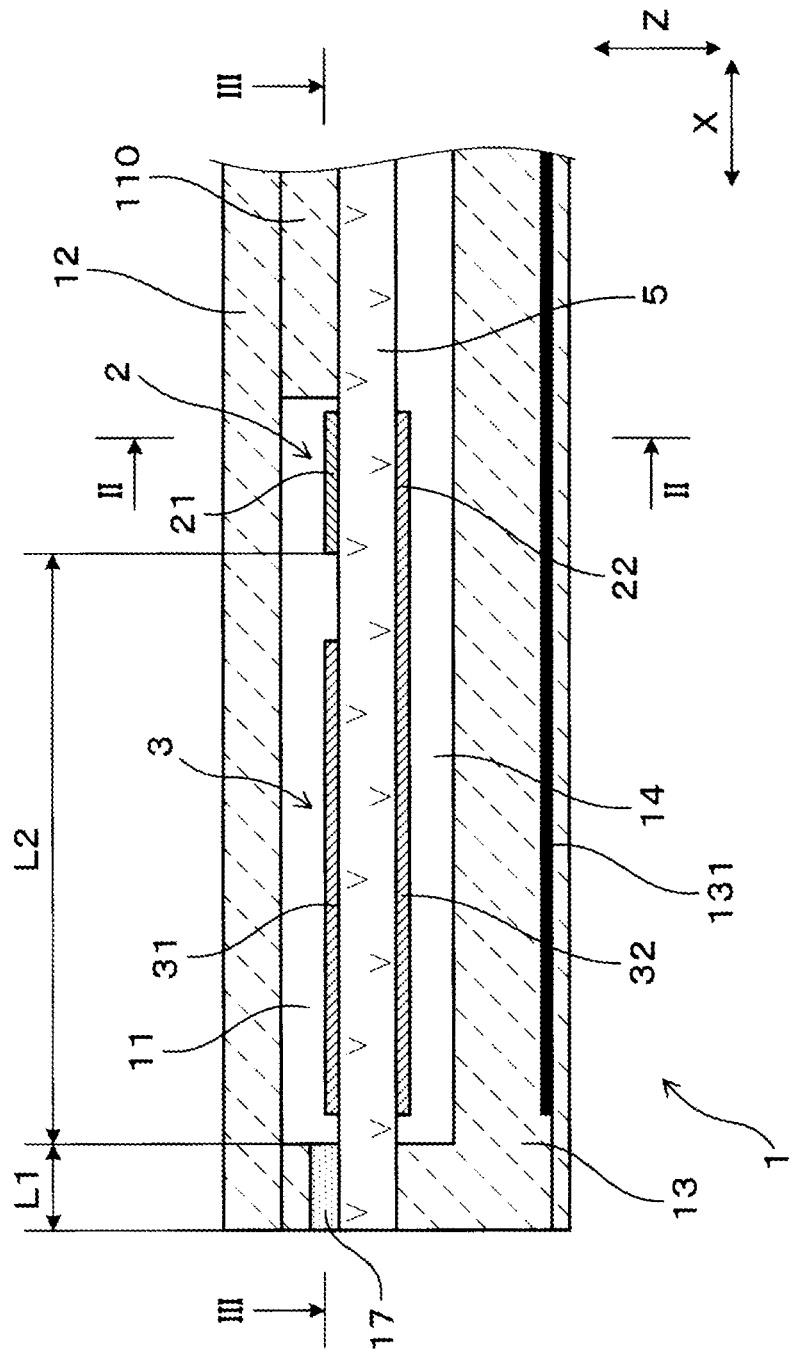
FIG. 1 is a sectional view as taken in an axial direction of a gas sensor device in the embodiment 1.
Figure 2:
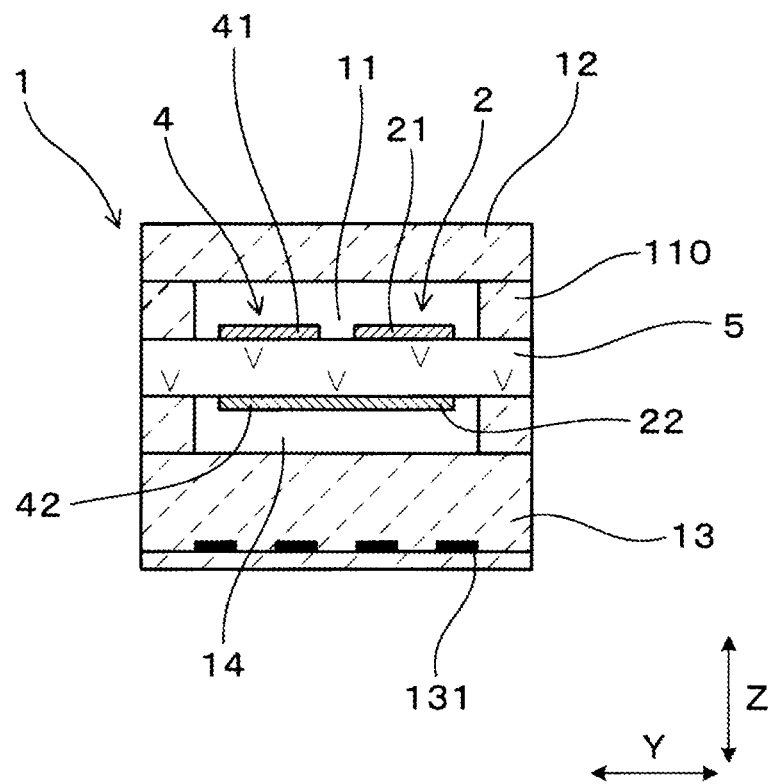
FIG. 2 is a sectional view as taken along the line II-II in FIG. 1.

The gas sensor device 1 of this embodiment, as illustrated in FIGS. 1 and 2, includes the solid electrolyte body 5 having oxygen ion conductivity, the sensor cell 2 which measures the concentration of a specified gas contained in a measurement gas, the pump cell 3 which regulates the concentration of oxygen in the measurement gas, the inner void space 11 into which the measurement gas is introduced, and the gas inlet 17 formed to provide a given diffusion resistance to a flow of the measurement gas entering the gas sensor device 1 (i.e., the inner void space 11) from outside it.

The sensor cell 2 is created by a portion of the oxygen ion conductive solid electrolyte body 5 and a pair of sensor electrodes 21 and 22 disposed on the solid electrolyte body 5.

The pump cell 3 is created by a portion of the solid electrolyte body 5 and a pair of pump electrodes 31 and 32 disposed on the solid electrolyte body 5 and configured to regulate the concentration of oxygen in the measurement gas.

The inner void space 11 faces the sensor electrode 21 and the pump electrode 31 and has the measurement gas introduced thereinto.

The gas inlet 17 is, as described above, constructed so that the measurement gas passes through the gas inlet 17 and enters the inner void space 11 and functions as a diffusion resistor to provide a given diffusion resistance to the measurement gas.

Figure 4:
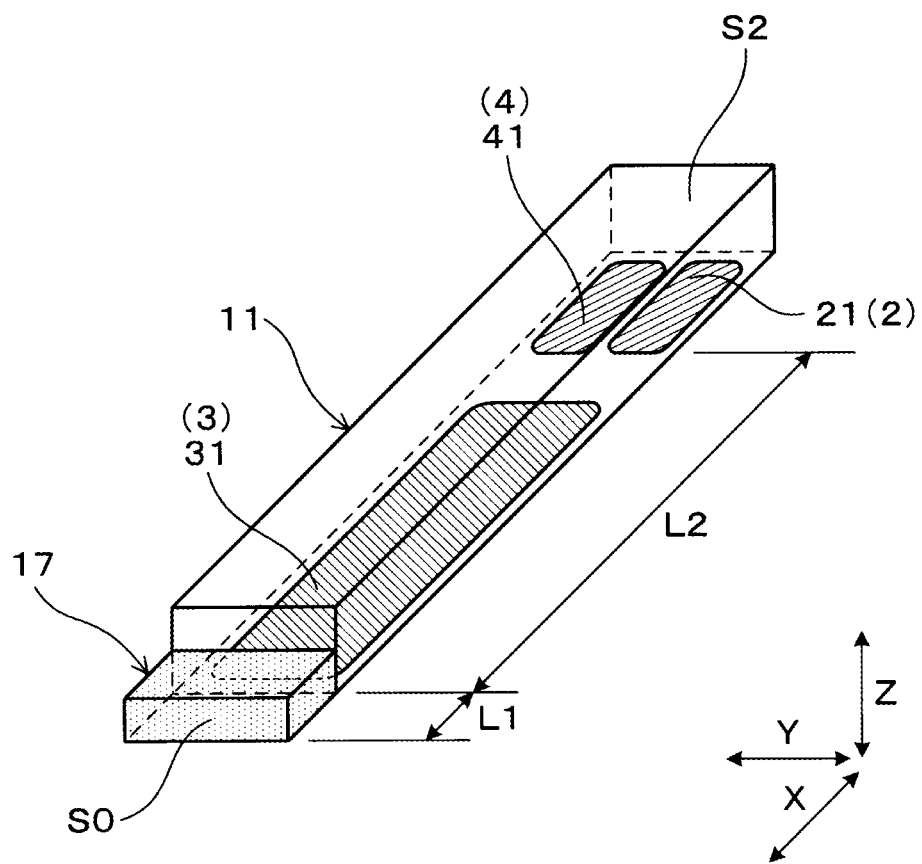
FIG. 4 is a perspective explanatory view of an inner void space and a gas inlet in the embodiment 1.

If a dimension of the gas inlet 17 in a direction of flow of the measurement gas in the gas inlet 17, as illustrated in FIGS. 1 and 4, (in other words, the distance the measurement gas travels within the gas inlet 17) is defined as L1, a section area of the gas inlet 17 taken in a direction perpendicular to the direction of flow of the measurement gas in the gas inlet 17 is defined as S1, the distance between the gas inlet 17 and the sensor cell 2 in the direction of flow of the measurement gas is defined as L2, and a sectional area of the inner void space 11 in a direction perpendicular to a direction in which the pump cell 3 and the sensor cell 2 are aligned is defined as S2, L1, S1, L2, and S2 are selected to meet a relation of $1000 \leq (L1/S1) \times (L2/S2) \leq 5000$ and more preferably meet a relation of $1250 \leq (L1/S1) \times (L2/S2) \leq 2500$.

The gas sensor device 1 of this embodiment is a NOx sensor working to measure the concentration of nitrogen oxide (NOx). Specifically, in this embodiment, the measurement gas is exhaust gas from an internal combustion engine of automotive vehicles, etc. The given gas component is NOx.

The gas sensor device 1 is, as illustrated in FIGS. 1 and 2, made of a stack of the solid electrolyte body 5, the spacer 110 for forming the inner void space 11, the insulating plate 12 which faces the solid electrolyte body 5 through the inner void space 11, and heater substrate 13 in which the heater 131 is disposed. The solid electrolyte body 5 is made of zirconia ($ZrO_2$). The spacer 110, the insulating plate 12, and the heater substrate 13 are each made of alumina ($Al_2O_3$).

The reference gas chamber 14 into which air that is a reference gas is introduced is formed between the heater substrate 13 and the solid electrolyte body 5. The spacer 110 has, as clearly illustrated in FIGS. 1 and 3, a front end in which a cut-out is partially formed as functioning as the gas inlet 17. In other words, the gas inlet 17 is formed in the front end of the gas sensor device 1.

In this embodiment, an alumina porous body is disposed in the gas inlet 17 to create a given diffusion resistance to the measurement gas. In other words, the gas inlet 17 is made of the alumina porous body. The above described sectional area S1 is, therefore, given by multiplying the sectional area S0 (see FIG. 4) of the gas inlet 17 (i.e., the porous body) by a porosity of the porous body. The sectional area S0 is a sectional area of the porous body taken in a direction perpendicular to the direction of flow of the measurement gas in the gas inlet 17. The porosity of the porous body may be measured by cutting the porous body to have a flat section and observing it using, for example, an SEM (Scanning Electron Microscope). More specifically, after gas cavities of the propos body are impregnated with a low-viscosity resin, the porous body is cut using a slicer to expose a flat cross section to be observed. Subsequently, the cross section is smoothed and then observed using the SEM. A percentage of an area of an aggregate appearing at the cross section is calculated by means of image processing. A value derived by subtracting such an area percentage from 100% is determined as the porosity of the porous body. The gas inlet 17 may alternatively be created by a void space (hole) without use of the porous body. In this case, the size and configuration of such a void space may be selected so as to provide a given diffusion resistance to the measurement gas flowing into the inner void space 11.

The inner void space 11 is, as clearly illustrated in FIG. 4, shaped to have a configuration uniform from a region where it faces the pump electrode 31 to a region where it faces the sensor electrode 21. In this embodiment, the inner void space 11 is in the form of a rectangular parallelepiped and has a substantially constant rectangular cross section taken perpendicular to the axial direction X from the front end to the base end thereof.

Figure 3:
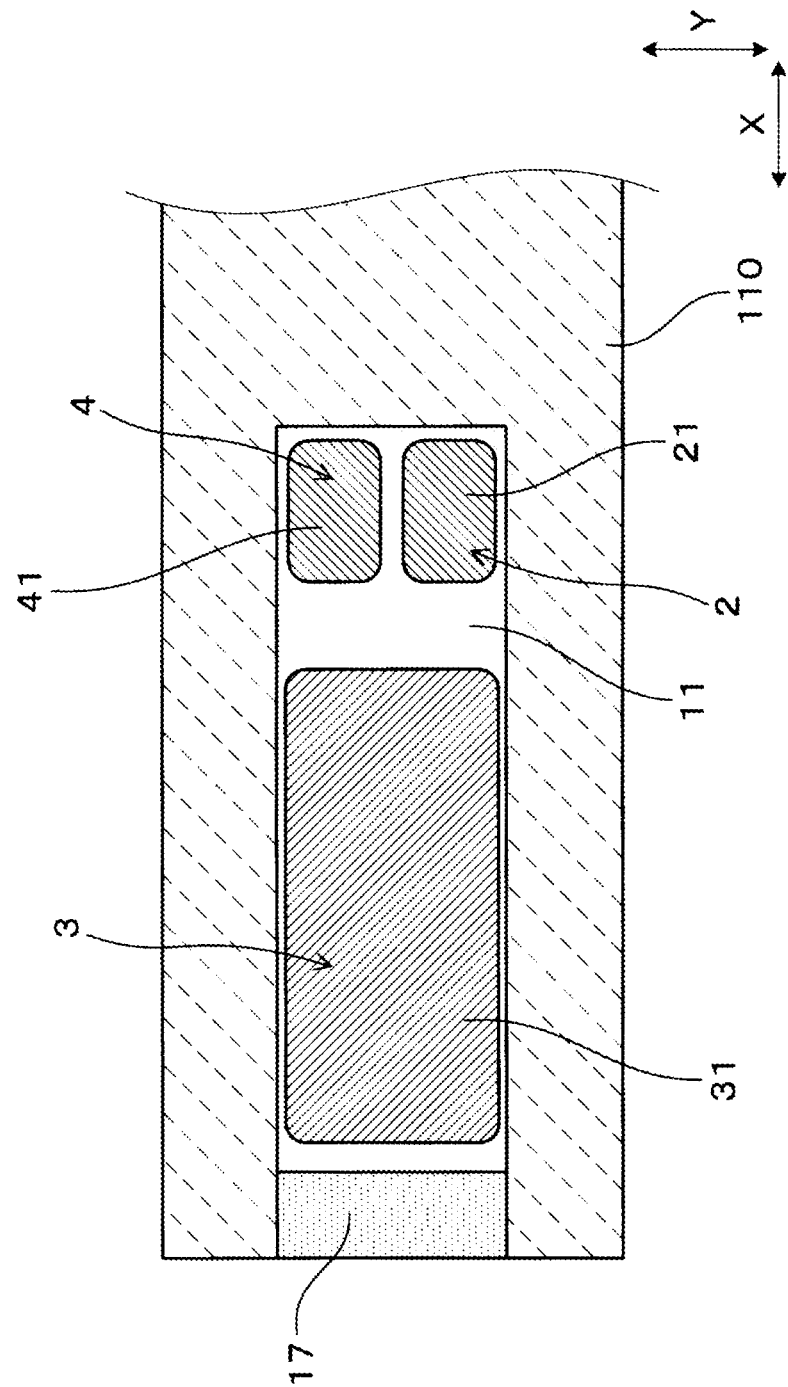
FIG. 3 is a sectional view as taken along the line III-III in FIG. 1.

The solid electrolyte body 5, as illustrated in FIGS. 1 and 3, has two major surfaces opposed to each other. The pump electrode 31 and the sensor electrode 21 which are disposed on one of the major surfaces of the solid electrolyte body 5 are arranged inside the inner void space 11. Similarly, the pump electrode 32 and the sensor electrode 22 which are formed on the other major surface of the solid electrolyte body 5 are arranged inside the reference gas chamber 14. In this embodiment, the pump electrode 32 and the sensor electrode 22 have a single common electrode.

The gas sensor device 1 also includes, as illustrated in FIGS. 2 and 3, the monitor cell 4 which works to measure the concentration of oxygen contained in the exhaust gas (i.e., the measurement gas). The monitor cell 4 is created by a portion of the solid electrolyte body 5 and a pair of monitor electrodes 41 and 42 disposed on the solid electrolyte body 5. Specifically, the monitor electrode 41 is arranged inside the inner void space 11 in addition to the pump electrode 31 and the sensor electrode 21. The monitor electrode 42 is disposed inside the reference gas chamber 14 in addition to the pump electrode 32 and the sensor electrode 22. The monitor electrode 42 forms a single common electrode along with the pump electrode 32 and the sensor electrode 22.

The direction in which the sensor cell 2 and the monitor cell 4 are aligned with each other is, as illustrated in FIG. 3, perpendicular to the direction in which the pump cell 3 and the sensor cell 2 are aligned with each other. In this embodiment, the direction in which the pump cell 3 and the sensor cell 2 are aligned with each other is the axial direction X of the gas sensor device 1. The direction in which the sensor cell 2 and the monitor cell 4 are aligned with each other is the width-wise direction Y which extends perpendicular both to the axial direction X of the gas sensor device 1 and to a stacking direction Z. The sensor cell 2 and the monitor cell 4 are arranged closer to the base end side than the pump cell 3 is. In other words, the sensor cell 2 and the monitor cell 4 are disposed on the opposite side of the pump cell 3 to the gas inlet 17 in the axial direction X. The locations of the sensor cell 2, the pump cell 3, and the monitor cell 4 are aligned with those of the sensor electrode 21, the pump electrode 31, and the monitor electrode 41.

In this embodiment, the sensor electrode 21, the monitor electrode 41, and the pump electrode 31 which faces the inner void space 11 are each made from alloy containing two or more kinds of metallic components. Specifically, the sensor electrode 21 is made from an alloy of Pt (Platinum) and Rh (Rhodium). Each of the monitor electrode 41 and the pump electrode 31 is made from an alloy of Pt and Au (Gold). The sensor electrode 21, thus, works to decompose NOx and oxygen molecules. The monitor electrode 41 and the pump electrode 31, thus, work to decompose oxygen molecules, but not to decompose NOx molecules.

The operation of the gas sensor device 1 will be described below.

The measurement gas is introduced into the inner void space 11 through the gas inlet 17. In this condition, the voltage is applied to the pump electrodes 31 and 32 of the pump cell 3, so that oxygen of the exhaust gas is reduced on the pump electrode 31 facing the inner void space 11 into oxygen ions which are then pumped to the pump electrode 32. The oxygen is, thus, discharged from the inner void space 11 into the reference gas chamber 14.

The application of a given voltage to the monitor electrodes 41 and 42 of the monitor cell 4 causes oxygen in the exhaust gas to be reduced on the motor electrode 41 facing the inner void space 11 into oxygen ions which are then pumped to the monitor electrode 42. The current flowing through the monitor cell 4 depends upon the concentration of oxygen in the measurement gas.

A given voltage is also applied to the sensor electrodes 21 and 22 of the sensor cell 2. This causes oxygen and nitrogen oxide contained in the exhaust gas within the inner void space 11 to be decomposed on the sensor electrode 21 into oxygen ions which are then pumped to the sensor electrode 22. The current flowing through the sensor cell 2 depends upon concentrations of oxygen and nitrogen oxide.

In the above way, the pump cell 3 works to keep the concentration of oxygen in the inner void space 11 and also to measure degrees of current flowing through the sensor cell 2 and the monitor cell 4, respectively. This enables the concentration of nitrogen oxide to be accurately calculated by a difference between the current value measured by the sensor cell 2 and that measured by the monitor cell 4.

The operation and beneficial effects of this embodiment will be described below.

The gas sensor device 1 is designed to have a relation of $1000 \leq (L1/S1) \times (L2/S2) \leq 5000$, thus ensuring compatibility between the responsiveness and the measurement accuracy.

The inventors of this application have focused on the fact that the responsiveness and the measurement accuracy greatly depend upon the structure of the gas inlet 17 as well as that of the inner void space 11 and studied, as indicated in experimental examples which will be discussed later, a relation of the product P of the first diffusion resistance indicator (L1/S1) and the second diffusion resistance indicator (L2/S2) to the responsiveness and the measurement accuracy. The inventors have found that the compatibility between the responsiveness and the measurement accuracy is achieved by setting the product of the first diffusion resistance indicator and the second diffusion resistance indicator, that is, (L1/S1)×(L2/S2) to 1000 to 5000 and that the compatibility between the responsiveness and the measurement accuracy may be enhanced by selecting a value of (L1/S1)×(L2/S2) to fall in a range of 1250 to 2500.

In this embodiment, the gas inlet 17 is, as described above, made of the porous body and has the sectional area S1 which is derived by a produce of the sectional area S0 of the gas inlet 17 and the porosity of the porous body. This facilitates adjustment of the diffusion resistance, as created in the gas inlet 17. The selection of (L1/S1)×(L2/S2) enables the responsiveness and the measurement accuracy to be accurately controlled.

The inner void space 11 is shaped to have a configuration uniform from a region where it faces the pump electrode 31 to a region where it faces the sensor electrode 21. This achieves a smooth travel of the measurement gas (i.e., exhaust gas), as introduced into the inner void space 11, to the sensor electrode 21, thereby enhancing the responsiveness of the gas sensor device 1.

The gas sensor device 1 is equipped with the monitor cell 4, thus improving the accuracy in measuring the concentration of a given gas component (i.e., NOx). The direction in which the sensor cell 2 and the monitor cell 4 are aligned with each other is perpendicular to that in which the pump cell 3 and the sensor cell 2 are aligned with each other, thereby further improving the measurement accuracy.

As apparent from the above discussion, this embodiment is capable of providing the gas sensor device which ensures the compatibility between the responsiveness and the measurement accuracy.

Experimental Example 1

In this example, we checked a relation of the product P of the first diffusion resistance indicator (L1/S1) and the second diffusion resistance indicator (L2/S2) to the measurement accuracy of the gas sensor device.

Specifically, the measurement accuracy was evaluated using a value of current flowing through the sensor cell 2. An offset current is current flowing through the sensor cell 2 when the measurement gas does not contain NOx gas (i.e., given gas component). The greater the offset current, the greater the measurement accuracy deteriorates.

We prepared a plurality of gas sensor devices for use in the experimental example 1 which are basically identical in structure with the gas sensor device 1 in the embodiment 1, but shaped to have values of the above product P different from each other. Specifically, the different values of the product P were derived by changing the distance L2 between the base end of the gas inlet 17 to the front end of the sensor cell 2 in the inner void space 11 and the sectional area S2.

We measured the offset current in each of the gas sensor devices. Specifically, we made gas sensors equipped with the respective gas sensor devices and installed them in an exhaust pipe in which the measurement gas flows. The measurement gas used in this experiment does not contain NOx, but contain 20% of oxygen.

Figure 5:
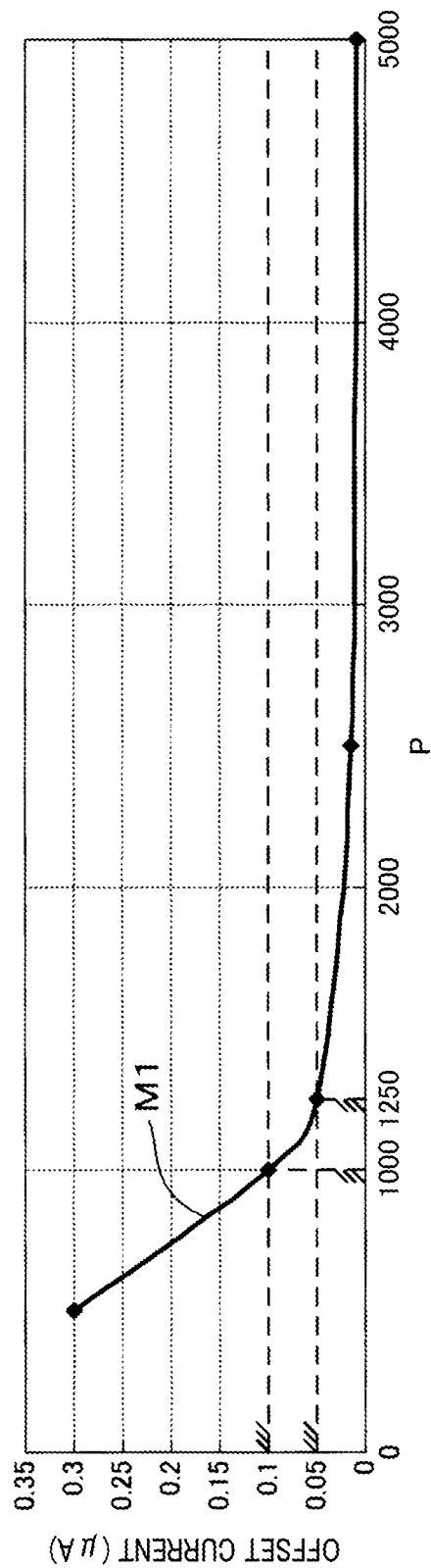
FIG. 5 is a diagrammatic view which represents a relation between a product P and an offset current in the experimental example 1.

Results of the measurement are shown in FIG. 5. In the graph of FIG. 5, five plots represent measured values. The curve M1 is an approximate curve derived along the measured values. The graph shows that the greater the product P, the smaller the offset current, when P≥1000, the offset current will be lower than or equal to 0.1 µA, and when P≥1250, the offset current will be lower than or equal to 0.05 µA. The measurement results show that the offset current is decreased by increasing the product P, thereby improving the measurement accuracy of the gas sensor devices, a desired degree of the measurement accuracy of the gas sensor devices is derived by meeting a relation of P≥1000, and further improvement of the measurement accuracy of the gas sensor devices is derived by meeting a relation of P≥1250.

Experimental Example 2

In this example, we checked a relation of the product P of the first diffusion resistance indicator (L1/S1) and the second diffusion resistance indicator (L2/S2) to the responsiveness of the gas sensor device.

Specifically, the measurement accuracy was evaluated using a value of current flowing through the sensor cell 2. An offset current is current flowing through the sensor cell 2 when the measurement gas does not contain NOx gas (i.e., given gas component). The greater the offset current, the greater the measurement accuracy deteriorates.

The evaluation of the responsiveness was made by measuring a time required by the gas sensor devices to respond to nitrogen oxide. We prepared a plurality of gas sensor devices for use in the experimental example 2 which are basically identical in structure with the gas sensor device 1 in the embodiment 1, but shaped to have values of the above product P different from each other.

We measured the response time of each of the gas sensor devices. Specifically, we made gas sensors equipped with the respective gas sensor devices and installed them in an exhaust pipe in which the measurement gas flows at a velocity of 12 m/s. We measured an output from the gas sensor and changed the concentration of NOx greatly at some point in time. A time interval between when the concentration of NOx changed and when the output of the gas sensor changed was measured as the response time.

Results of the measurement are shown in FIG. 6. In the graph of FIG. 6, five plots represent measured values. The curve M2 is an approximate curve derived along the measured values. The graph shows that the smaller the product P, the shorter the response time, when P≤5000, the response time will be lower than or equal to 0.5 sec., and when P≤2500, the response time will be lower than or equal to 0.3 sec. The measurement results show that the response time is shortened by decreasing the product P, thereby improving the measurement accuracy of the gas sensor devices, a desired value of the response time of the gas sensor devices is obtained by meeting a relation of P≤5000, and further shortening of the response time of the gas sensor devices is derived by meeting a relation of P≤2500.

The gas sensor device 1 of this embodiment may be modified in various ways.

For instance, the embodiment 1 has showed an example where the gas inlet 17 is made of the porous body, but however, the gas inlet 17 may alternatively be shaped to have a sectional area which extends perpendicular to the direction in which the measurement gas flows and is smaller than that of the inner void space 11 without use of the porous body. Further, the embodiment 1 has showed an example where the gas inlet 17 is located closer to the top end of the gas sensor device 1 than the inner void space 11 is, but however, the gas inlet 17 may alternatively be arranged at a location where it communicates with the inner void space 11 in the stacking direction Z (i.e., the thickness-wise direction) or in the width-wise direction Y. In such a case, the dimension L1 is a dimension of the gas inlet 17 in the stacking direction (i.e. the thickness-wise direction) or the width-wise direction Y. In other words, the dimension L1 is a dimension of the gas inlet 17 in the direction of flow of the gas.

The invention claimed is:

1. A gas sensor device comprising:
a sensor cell which is made up of a first portion of an oxygen ion conductive solid electrolyte body and a pair of sensor electrodes disposed on the solid electrolyte body, the sensor cell working to measure a concentration of a given gas component in a measurement gas;
a pump cell which is made up of a second portion of the solid electrolyte body and a pair of pump electrodes disposed on the solid electrolyte body, the pump cell working to regulate a concentration of oxygen in the measurement gas;
an inner void space which faces one of the sensor electrodes and one of the pump electrodes and into which the measurement gas is introduced; and
a diffusion resistor through which the measurement gas is introduced into said inner void space and which is shaped to provide a given diffusion resistance to the measurement gas introduced into said inner void space,
wherein if a dimension of said diffusion resistor in a direction in which the measurement gas flows in said diffusion resistor is defined as L1, a sectional area of said diffusion resistor taken perpendicular to the direction of flow of the measurement gas in said diffusion resistor is defined as S1, a distance between said diffusion resistor and said sensor cell is defined as L2, and a sectional area of said inner void space taken perpendicular to a direction in which said pump cell and said sensor cell are aligned with each other is defined as S2, a relation of $1000 \leq (L1/S1) \times (L2/S2) \leq 5000$ is met, and the product of $(L1/S1) \times (L2/S2)$ has the unit of 1/length unit$^2$,
in that the above diffusion resistor is made of a porous body, and said sectional area S1 is a value derived by a product of a sectional area of the porous body taken perpendicular to the direction of flow of the measurement gas and a porosity of the porous body, and
in that said inner void space is shaped to have a configuration uniform from a region where the inner void space faces the pump electrode to a region where the inner void space faces the sensor electrode;
wherein a direction in which said sensor cell and a monitor cell are aligned with each other is perpendicular to a direction in which said pump cell and said sensor cell are aligned with each other.

2. A gas sensor device as set forth in claim 1, wherein a relation of $1250 \leq (L1/S1) \times (L2/S2) \leq 2500$ is met.

3. A gas sensor device as set forth in claim 1, wherein the monitor cell is made up of a portion of said solid electrolyte body and a pair of monitor electrodes disposed on the solid electrolyte body and works to measure a concentration of oxygen in the measurement gas.

* * * * *